US007226620B2

(12) United States Patent
Hendricks et al.

(10) Patent No.: US 7,226,620 B2
(45) Date of Patent: Jun. 5, 2007

(54) DIRECTLY COMPRESSIBLE TRICALCIUM PHOSPHATE

(75) Inventors: Lewis Roe Hendricks, Richboro, PA (US); Jill Marie Jobbins, Freehold, NJ (US); Wayne Camarco, Hoboken, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 11/122,151

(22) Filed: May 4, 2005

(65) Prior Publication Data

US 2005/0249813 A1    Nov. 10, 2005

Related U.S. Application Data

(60) Provisional application No. 60/567,926, filed on May 4, 2004.

(51) Int. Cl.
| | |
|---|---|
| A61K 9/68 | (2006.01) |
| A61K 9/14 | (2006.01) |
| A61K 9/16 | (2006.01) |
| A61K 9/20 | (2006.01) |
| A61K 33/42 | (2006.01) |
| A61K 47/02 | (2006.01) |
| A61K 47/06 | (2006.01) |
| A61K 47/22 | (2006.01) |
| A61K 47/26 | (2006.01) |
| A61K 47/36 | (2006.01) |

(52) U.S. Cl. .................. 424/496; 424/441; 424/464; 424/489; 424/490; 424/493; 424/497; 424/602; 514/769; 514/772; 514/772.3; 514/777; 514/782; 514/951; 514/952; 514/960

(58) Field of Classification Search ............... 424/464, 424/489, 493, 496, 497, 500, 501, 602, 441, 424/490; 514/950, 951, 961, 769, 772, 772.3, 514/777, 782, 952, 960
See application file for complete search history.

(56) References Cited

U.S. PATENT DOCUMENTS

| | | | | |
|---|---|---|---|---|
| 3,134,719 | A | 5/1964 | Seth et al. | 167/82 |
| 3,424,842 | A | 1/1969 | Nurnberg | 424/94 |
| 3,639,168 | A | 2/1972 | Monti et al. | 127/29 |
| 3,639,169 | A | 2/1972 | Broeg et al. | 127/29 |
| 3,821,414 | A | 6/1974 | Monti | 424/361 |
| 5,490,990 | A * | 2/1996 | Grabowski et al. | 424/486 |
| 6,235,322 | B1 | 5/2001 | Lederman | 426/74 |
| 2002/0086094 | A1 | 7/2002 | Buddemeyer et al. | 426/73 |
| 2003/0031726 | A1 * | 2/2003 | Hendricks | 424/602 |

FOREIGN PATENT DOCUMENTS

| | | | |
|---|---|---|---|
| CA | 1325707 | | 7/1987 |
| EP | 265951 | * | 5/1988 |

* cited by examiner

Primary Examiner—John Pak

(57) ABSTRACT

A compressible tricalcium phosphate agglomerate comprises tricalcium phosphate particles, each having an outer surface, and a binder comprising a polyvinylpyrollidone, carrageenan, or a guar gum, supported on at least a portion of the outer surface of at least a portion of the tricalcium phosphate particles.

17 Claims, No Drawings

US 7,226,620 B2

DIRECTLY COMPRESSIBLE TRICALCIUM PHOSPHATE

This application claims benefit of Provisional Application 60/567,926, filed on May 4, 2004.

FIELD OF THE INVENTION

This invention relates to tricalcium phosphate for use in directly compressible tablet formulations.

BACKGROUND OF THE INVENTION

Tricalcium phosphate is widely used as an excipient in pharmaceutical applications.

Recent studies that establish the value of mineral dietary supplements that supply both calcium and phosphorus has given rise to an interest in making oral dosage forms, such as tablets or caplets and including chewable oral dosage forms such as chewable tablets, wherein calcium phosphate is the main ingredient.

However, attempts to use tricalcium phosphate as the main ingredient in oral dosage forms have resulted in tablets that exhibit an undesirably low hardness. Moreover, chewable tablets made using calcium phosphates exhibit undesirable mouth feel described as "gritty" and or "chalky".

What is needed is a way to make oral dosage forms that contain a high relative amount of tricalcium phosphate and that exhibit good properties, including acceptable hardness. A further need is for such tablets, if designed to be chewable tablets, to have acceptable sensory qualities, including good mouthfeel, lack of grittiness, and lack of chalkiness.

SUMMARY OF THE INVENTION

In a first aspect, the present invention is directed to a compressible tricalcium phosphate agglomerate, comprising: tricalcium phosphate particles, each having an outer surface, and a binder comprising a polyvinylpyrollidone, carrageenan, or a guar gum, supported on at least a portion of the outer surface of at least a portion of the tricalcium phosphate particles.

In a second aspect, the present invention is directed to a process for making a compressible tricalcium phosphate agglomerate, comprising spray drying an aqueous solution of tricalcium phosphate and a binder comprising a polyvinylpyrollidone, carrageenan, or a guar gum.

In a third aspect, the present invention is directed to a directly compressible calcium dietary supplement composition, comprising, based on 100 parts by weight ("pbw") of the composition:

from about 20 to about 80 pbw of an agglomerate, comprising tricalcium phosphate particles, each having an outer surface, and a binder comprising a polyvinylpyrollidone, carrageenan, or a guar gum, supported on at least a portion of the outer surface of at least a portion of the tricalcium phosphate particles, from about 79 to about 10 pbw of particles of a calcium-containing material other than the agglomerate, from about 0.5 to about 8 pbw of a disintegrant, and from about 0.5 to about 2 pbw of a lubricant.

In a fourth aspect, the present invention is directed to a process for making an oral dosage form of a calcium dietary supplement composition, comprising compressing the above described directly compressible calcium dietary supplement composition.

In a fifth aspect, the present invention is directed to an oral dosage form of a calcium dietary supplement composition, made by compressing the above described directly compressible calcium dietary supplement composition.

DETAILED DESCRIPTION OF INVENTION AND PREFERRED EMBODIMENTS

Any tricalcium phosphate that meets the specifications of US Pharmacopoeia, Vol. 26 ("USP/NF 26") or the Food Chemical Codex $5^{th}$ Edition (National Academy of Sciences, Washington, D.C.) ("FCC $5^{th}$ Ed.") is suitable for use as a component of the agglomerates of the present invention. In one embodiment, the tricalcium phosphate particles exhibit a particle size distribution wherein less than or equal to 2% by weight ("wt %"), more typically less than or equal to 0.6 wt %, of the particles have a particle size of greater than 140 mesh (about 100 μm) and less than or equal to 5 wt %, more typically less than or equal to 2 wt %, of the particles have a particle size of less than 325 mesh (about 50 μm).

As used herein, "binder" means any substance that is capable of rendering the mixture of acidic component and basic component of the composition of the present invention compactable into a solid, coherent mass. Suitable binder compounds include, for example, polyvinylpyrrolidones, guar gum, acacia, tragacanth, gelatin, polysaccharides such as glucose and sucrose, starch, pregelatinized starch, carrageenan, and cellulosic materials including methylcellulose and carboxymethylcellulose, as well as hydroxyalkyl cellulose compounds such as hyrodroxypropyl methylcellulose, hydroxypropyl cellulose and hydroxyethyl cellulose, as well as mixtures of any of the above.

In one embodiment, polyvinyl pyrrolidone is used as the binder. Suitable polyvinylpyrrolidones are those having a number average molecular weight of greater than or equal to about 30,000. In one embodiment, the polyvinylpyrrolidone binder has a number average molecular weight (Mw) of about greater than or equal to about 60,000, more typically greater than or equal to about 80,000.

In another embodiment, guar gum, a modified guar gum, or a mixture thereof is used as the binder. Guar gum refers to the water soluble fraction of ground endosperms of the leguminous plant Cyamopsis tetragonolobus. The gum consists of linear chains of (1,4)-.beta.-D mannopyranosyl units—with α D-galactopyranosyl units attached by (1,6) linkages, with a ratio of D-galactose to D-mannose of about 1:2. Guar gum may take the form of a whitish powder which is dispersible in hot or cold water. Modified guar gums include, for example carboxymethyl guar, carboxymethylhydroxypropyl guar, cationic hydroxpropyl guar, hydroxyalkyl guar, including hydroxyethyl guar, hydroxypropyl guar, hydroxybutyl guar and higher hydroxylalkyl guars, carboxylalkyl guars, including carboxymethyl guar, carboxylpropyl guar, carboxybutyl guar, and higher alkyl carboxy guars. Suitable guar gums are those guar gums and modified guar gums that meet FCC, $5^{th}$ Edition specifications and form solutions having a sufficiently low viscosity to allow use in a spray drying process. In one embodiment, the guar gum has an average molecular weight of less than or equal to about 2,000,000 daltons, more typically, a number average molecular weight of from about 200,000 daltons to about 2,000 daltons.

In one embodiment, the agglomerate of the present invention comprises, based on 100 pbw of the composition:

from about 90 to about 99 pbw, more typically from about 93 to about 98 pbw, and still more typically from about 95 to about 97 pbw, tricalcium phosphate, and from about 10 to about 1 pbw, more typically from about 7 to about 2 pbw, and still more typically from about 5 to about 3 pbw, binder.

The agglomerate of tricalcium phosphate and binder may be made by any suitable agglomeration technique, including agitation agglomeration techniques, such as fluidized bed drying and high shear mixing, pressure agglomeration techniques, such as compression, or spray agglomeration techniques, such as spray drying.

In one embodiment, an agglomerate of tricalcium phosphate and binder is made by spray drying an aqueous solution of calcium phosphate and a binder.

In one embodiment, the agglomerate particles exhibit a particle size distribution wherein less than or equal to 65 percent by weight ("wt %"), more typically 90 wt %, of the particles have a particle size of greater than 325 mesh (about 50 μm) and less than or equal to 10 wt %, more typically 2 wt %, of the particles have a particle size of less than 60 mesh (about 200 μm).

The agglomerate of tricalcium phosphate and binder may be blended with other ingredients, such as, for example, particles calcium-containing materials, lubricants, disintegrants, and flow agents, in a suitable mixer, to provide the directly compressible tricalcium phosphate composition of the present invention.

In one embodiment, the directly compressible calcium dietary supplement composition of the present invention further comprises particles of one or more calcium-containing materials other than the agglomerate of the present invention. Suitable calcium-containing materials include, calcium chelates, such as for example, calcium proteinate, and calcium salts, such as, for example, calcium carbonate, calcium gluconate, calcium citrate, tricalcium phosphate, or dicalcium phosphate dihydrate or anhydrous dicalcium phosphate, and calcium citrate maleate.

In a one embodiment, the composition comprises tricalcium phosphate particles that exhibit a particle size distribution wherein less than or equal to 15 wt %, more typically 2.6 wt %, of the particles have a particle size of greater than 40 mesh (about 300 μm) and less than or equal to 5 wt %, more typically 0.9 wt %, of the particles have a particle size of less than 325 mesh (about 50 μm).

In one embodiment, the directly compressible calcium dietary supplement composition of the present invention further comprises a lubricant. As used herein, "lubricant" means a substance that reduces friction between the composition of the present invention and the surfaces of the apparatus used to compact the composition into a compressed form. Suitable lubricants include, for example, fatty acids, such as palmitic acid, stearic acid, oleic acid, hydrogenated vegetable oils, triglycerides of fatty acids, metal salts of fatty acids, such as for example, zinc stearate and magnesium stearate, glycols, such as polyethylene glycol, and talc, as well as mixtures thereof. In one embodiment, the lubricant component of the composition of the present invention comprises magnesium stearate.

In one embodiment, composition of the present invention comprises, based on 100 pbw of the composition, from about 0.05 to about 5 pbw, more typically from about 0.1 to about 3 pbw and still more typically from about 0.2 to about 2 pbw of a lubricant.

In one embodiment, the directly compressible calcium dietary supplement composition of the present invention further comprises a disintegrant. As used herein, "disintegrant" means a substance that is substantially insoluble in water, but that is capable of swelling in water. Disintegrants serve to accelerate the disintegration and dissolution in an aqueous medium of compressed forms of the composition of the present invention. Any pharmaceutically acceptable compound that is substantially insoluble in water but capable of swelling in water in order to accelerate the disintegration and dissolution in an aqueous medium of compressed dosage forms, e.g., tablets, formed from the composition of the present invention is suitable as the disintegrant of the composition of the present invention. Suitable disintegrants include, for example, sodium carboxylmethyl cellulose, starches, microcrystalline cellulose, soy protein, alginic acid, crosslinked polyvinylpyrrolidone, also known as crosslinked povidone, and crosslinked sodium carboxymethylcellulose, also known as croscarmellose sodium, as well as mixtures thereof. In one embodiment, the disintegrant of the composition of the present invention comprises croscarmellose sodium.

In one embodiment, the composition of the present invention comprises, based on 100 pbw of the composition, from about 0.05 to about 5, more typically from about 0.1 to about 4 pbw of a disintegrant.

In one embodiment, the directly compressible calcium dietary supplement composition comprises based on 100 pbw of the composition:

from about 15 to about 75 pbw, more typically from about 30 to about 60 pbw, of an agglomerate according to the present invention, from about 85 to about 25 pbw, more typically from about 70 to about 40 pbw, of particles of a calcium-containing material, typically tricalcium phosphate, other than the agglomerate, from about 0.05 to about 5, more typically from about 0.1 to about 4 pbw, of a disintegrant, and from about 0.05 to about 5 pbw, more typically from about 0.1 to about 3 pbw, and still more typically from about 0.2 to about 2 pbw, of a lubricant.

The directly compressible calcium dietary supplement composition of the present invention is useful to make finished oral dosage forms, such as, for example, tablets and caplets, by conventional methods, such as for example, using a tablet press, and is resistant to capping.

Oral dosage forms of the present invention exhibit high hardness, low friability and good disintegration properties. Chewable tablet dosage forms of the present invention exhibit very good mouthfeel and very low chalkiness and grittiness.

Hardness, as referred to herein, is measured using a Schleuniger Model 2E Tablet Hardness Tester.

In one embodiment, the oral dosage form of the present invention exhibits an hardness of greater than or equal to 15 kilopond ("kp"), more typically, from about 20 to about 30 kp, even more typically from about 24 to about 28 kp.

In another embodiment, the oral dosage form of the present invention is a chewable tablet exhibits a hardness of greater than or equal to 10 kp, more typically, from about 12 to about 22 kp, even more typically from about 14 to about 16 kp.

Friability, as referred to herein, is measured according to US Pharmacopoeia 1216 Tablet Friability test (USP 25) and is expressed as an attrition rate. In one embodiment, the oral dosage form of the present invention exhibits a friability of less than 1%, more typically less than about 0.6%, even more typically less than about 0.2%.

As referred to herein, "disintegration" is measured according to US Pharmacopoeia test method number 701 (USP 26) and is expressed as the time, in seconds, that is required for a tablet to disintegrate into smaller fragments that pass through a test screen when immersed in water at 37+/−2 degrees C. using the specified apparatus. In one embodiment, the oral dosage form of the present invention exhibits a disintegration of 90 seconds, more typically less than 60 seconds.

As used herein, the term "capping" means the loss of physical integrity of the tablet by separation of a tablet fragment or lamination of the tablet body after compression.

EXAMPLES 1–3

The compressible tricalcium phosphate agglomerates of Examples 1–3 were each made by spray drying a slurry comprising, on the basis of 100 pbw of slurry, 33.6 pbw tricalcium phosphate ("TCP") particles, 64.2 pbw water, and 2.2 pbw of one of three binders that is, polyvinyl pyrrollidone K30 ("PVP30"), polyvinyl pyrrollidone K90 ("PVP90"), or guar gum.

The spray drying was conducted in a Niro Mobile Minor laboratory scale spray drier using the following conditions:

| Damper | 100% open |
| Atomizer | Turbine |
| Air pressure | 4 kg/cm$^2$ |
| Heat | Setting II |
| Timer | 100% |

The particle size distributions for the tricalcium phosphate particles and for each of the agglomerates are set forth below in Table I.

TABLE I

| | | (TCP alone) | Ex. 1 | Ex. 2 | Ex. 3 |
|---|---|---|---|---|---|
| Binder | | — | PVP30 | PVP90 | Guar |
| Flowrate (g/s) | | | 19.7 | 37.3 | 22.3 |
| Bulk density (g/ml) | | 0.391 | 0.512 | 0.436 | 0.463 |
| Tap density (g/ml) | | 0.536 | 0.640 | 0.545 | 0.634 |
| Particle size (% cumulative retain) | | | | | |
| US Mesh | (μm) | | | | |
| 60 | | 0 | 0.1 | 0.1 | 0.1 |
| 80 | | 0.1 | 0.1 | 0.1 | 0.1 |
| 100 | | 0.1 | 0.1 | 0.1 | 0.1 |
| 140 | | 65.6 | 0.1 | 0.1 | 0.1 |
| 200 | | 85.6 | 0.1 | 0.1 | 0.1 |
| 270 | | 96.8 | 7.2 | 4 | 22.8 |
| 325 | | 98.4 | 14.4 | 12 | 36 |
| Pan | | — | 100 | 100 | 100 |

EXAMPLES 1B–3B AND COMPARATIVE EXAMPLE C1B

The agglomerates of Examples 1–3 were mixed with tricalcium phosphate, a disintegrant (AC-DI-SOL, manufactured by FMC Biopolymer Inc.), and a lubricant (magnesium stearate) in the relative amounts. (each given as pbw ingredient/100 pbw formulation) set forth below in Table II to make the directly compressible formulations of Comparative Example C1B, and Examples 1B, 2B, and 3B.

TABLE II

| | CEx. C1B | EX. 1B | Ex. 2B | Ex. 3B |
|---|---|---|---|---|
| TCP | 97.47 | 82.36 | 82.36 | 82.36 |
| TCP-C (Ex. 1) | — | 15.11 | — | — |
| TCP-C (Ex. 2) | — | — | 15.11 | — |
| TCP-C (Ex. 3) | — | — | — | 15.11 |
| disintegrant (AC-DI-SOL) | 2.02 | 2.02 | 2.02 | 2.02 |
| Magnesium stearate | 0.51 | 0.51 | 0.51 | 0.51 |
| Total | 100 | 100 | 100 | 100 |

EXAMPLES 1C–3C AND COMPARATIVE EXAMPLE C1C

The directly compressible compositions of Comparative Example C1B and Examples 1B, 2B, and 3B were each compressed in 0.312"×0.750" cylindrical molds in a tablet press (Manesty Betapress) to make the tablets of Comparative Example C1C and Examples 1C, 2C and 3C.

The hardness of the tablets was measured using a Schleuniger Model 2E Tablet Hardness Tester and is expressed in kiloponds (kp).

The friability of the tablets was measured according to US Pharmacopoeia 1216 Tablet Friability test (USP 25) and is expressed as % attrition.

The disintegration of the tablets was measured according to US Pharmacopoeia test method number 701 (USP 26) and is expressed as the time, in seconds, that is required for a tablet to disintegrate into smaller fragments that pass through a test screen when immersed in water at 37+/−2 degrees C. using the specified apparatus.

The tableting conditions, % capping, and tablet properties, that is, thickness, hardness, friability, and disintegration, for each of Comparative Example C1C and Examples 1C, 2C, and 3C, each under several different tableting conditions are set forth below in Tables III-VI.

TABLE III

| | Comparative Example C1C | | | |
|---|---|---|---|---|
| Preload (lb) | 400 | 800 | 800 | 800 |
| Force (tons) | 1.5 | 2.0 | 2.5 | 3.0 |
| Ejection Force (lb) | 80 | — | — | — |
| Tablet Properties | | | | |
| Weight (mg) | 1361 | 1363 | 1362 | |
| Hardness (kp) | 6.6 | 10.0 | 10.3 | — |
| Thickness (in) | 0.303 | 0.295 | 0.291 | |
| Friability (%) | — | — | — | — |
| Capping(%) | 0 | 1 | 98 | — |

TABLE IV

| | Example 1C | | | |
|---|---|---|---|---|
| Preload (lb) | 400 | 800 | 800 | 800 |
| Force (tons) | 1.5 | 2.0 | 2.5 | 3.0 |
| Ejection Force (lb) | — | — | — | — |
| Tablet Properties | | | | |
| Weight (mg) | 1356 | 1375 | 1385 | 1395 |
| Hardness (kp) | 7.9 | 10.9 | 13.2 | 16.5 |
| Thickness (in) | 0.303 | 0.300 | 0.293 | 0.289 |
| Friability (%) | — | — | — | — |
| Capping(%) | 0 | 0 | 0 | 1 |

TABLE V

| | | Example 2C | | |
|---|---|---|---|---|
| Preload (lb) | 400 | 800 | 800 | 800 |
| Force (tons) | 1.5 | 2.0 | 2.5 | 3.0 |
| Ejection Force (lb) | — | 100 | 100 | 100 |
| Tablet Properties | | | | |
| Weight (mg) | — | 1361 | 1358 | 1358 |
| Hardness (kp) | — | 11.9 | 14.4 | 19.0 |
| Thickness (in) | — | 0.299 | 0.284 | 0.283 |

TABLE V-continued

| | | Example 2C | | |
|---|---|---|---|---|
| Friability (%) | — | 0.23 | 0.16 | 0.14 |
| Capping (%) | — | 0 | 0 | 0 |
| Disintegration (s) | — | 31 | 33 | 38 |

TABLE VI

| | | Example 3C | | |
|---|---|---|---|---|
| Preload (lb) | 400 | 800 | 800 | 800 |
| Force (tons) | 1.5 | 2.0 | 2.5 | 3.0 |
| Ejection Force (lb) | — | 100 | 100 | 100 |
| Tablet Properties | | | | |
| Weight (mg) | — | 1361 | 1362 | 1364 |
| Hardness (kp) | — | 11.1 | 14.6 | 17.0 |
| Thickness (in) | — | 0.303 | 0.291 | 0.287 |
| Friability (%) | — | 0.25 | 0.16 | 0.13 |
| Capping (%) | — | 0 | 0 | 0 |
| Disintegration (s) | — | 32 | 41 | 46 |

The results show increased hardness of tablets comprising the tricalcium phosphate agglomerate of the present invention, compared to analogous tablets made with conventional tricalcium phosphate.

EXAMPLE 4

The directly compressible composition of Example 4A was by mixing:
  45.41 pbw of an agglomerate made according to the process described above in Example 3,
  47.68 pbw TRI-TAB™ tricalcium phosphate (Rhodia Inc.),
  4.01 additional binder (carboxymethyl cellulose (PH102) FMC Corp.),
  0.17 pbw Vitamin $D_3$ 100,
  2.02 pbw disintegrant ("AC-DI-SOL", FMC Corp.),
  0.24 pbw sodium lauryl sulfate, NF 21(SLS, Stepanol WA-100 (Stepan Corp.)), and
  0.48 pbw lubricant (magnesium stearate).

The mixture of Example 4A was compressed according in a tablet press (Manesty Betapress) using 0.312"×0.750" caplet punches to make the caplets of Example 4B.

The hardness, thickness, friability, capping, and disintegration performance of the caplets of Example 4B were each tested according to the methods set forth above in Examples 1C–3C and Comparative Example C1C. The tabletting conditions and test results are set forth below in TABLE V.

TABLE V

| | | | Example 4B | | |
|---|---|---|---|---|---|
| Force (tons) | 1.0 | 1.5 | 2.0 | 2.5 | 3.0 |
| Ejection Force (lb) | 70 | 100 | 120 | 140 | 160 |
| Tablet Properties | | | | | |
| Weight (mg) | 1414 | 1412 | 1415 | 1413 | 1413 |
| Hardness (kp) | 14.7 | 19.9 | 27.3 | 28.8 | 31.8 |
| Thickness (in) | 0.331 | 0.316 | 0.304 | 0.296 | 0.290 |
| Friability (%) | 0.355 | 0.247 | 0.195 | 0.176 | 0.177 |
| Capping(%) | 0 | 0 | 0 | 0 | 0 |
| Disintegration (s) | 25 | 34 | 38 | 42 | 46 |

EXAMPLE 5

The chewable tablets of Example 5, each nominally ⅝" in diameter, 0.3" thick and 2000 mg in weight, were made by compressing a mixture of:
  42.59 pbw of an agglomerate made according to the procedure set forth above for Example 1,
  51.69 pbw of an additional binder (Xylitab 200 (Danisco)),
  1.74 pbw flavoring (SD Cherry N&A (Virginia Dare)),
  1.74 pbw Prosweet #875 (Virginia Dare)
  0.16 pbw Aspartame™ (Searle), and
  2.06 pbw magnesium stearate.

in a tablet press ("D" Express Press) using ⅝" round flat faced tooling.

The tablets of Example 5 exhibited a hardness of 12.5 kp, measured as set forth above in Examples 1C–3C and Comparative Example C1C.

The tablets of Example 5 were found to exhibit minimal grittiness and chalky taste in an informal taste test.

The invention claimed is:

1. A compressible tricalcium phosphate agglomerate, comprising, based on 100 pbw of the agglomerate: from about 90 to about 99 pbw tricalcium phosphate particles, each having an outer surface, and from about 1 to about 10 pbw a binder comprising a polyvinylpyrrolidone, carrageenan, guar gum, modified guar gum, or a mixture of guar gum and modified guar gum, supported on at least a portion of the outer surface of at least a portion of the tricalcium phosphate particles, and made by spray drying an aqueous slurry comprising the tricalcium phosphate particles and the binder.

2. The agglomerate of claim 1, wherein the binder comprises polyvinyl pyrrolidone having a number average molecular weight of greater than or equal to about 30,000.

3. The agglomerate of claim 1, wherein the binder comprises guar gum, a modified guar gum or a mixture thereof.

4. A directly compressible calcium dietary supplement composition, comprising, based on 100 pbw of the composition:
- from about 20 to about 80 pbw of an agglomerate, according to claim 1,
- from about 79 to about 10 pbw of particles of one or more calcium-containing materials other than the agglomerate,
- from about 0.5 to about 8 pbw of a disintegrant, and
- from about 0.5 to about 2 pbw of a lubricant.

5. The composition of claim 4, wherein the particles of one or more calcium-containing materials other than the agglomerate are selected from the group consisting of calcium chelates, calcium salts, and mixtures thereof.

6. The composition of claim 4, wherein the particles of one or more calcium-containing materials other than the agglomerate comprise tricalcium phosphate particles that exhibit a particle size distribution wherein less than or equal to 15 percent by weight of the particles have a particle size of greater than 40 mesh and less than or equal to 5 percent by weight of the particles have a particle size of less than 325 mesh.

7. The composition of claim 4, wherein the lubricant is selected from the group consisting of fatty acid, hydrogenated vegetable oils, triglycerides of fatty acids, metal salts of fatty acids, glycols, talc, and mixtures thereof.

8. The composition of claim 4, wherein the disintegrant is selected from the group consisting of sodium carboxylmethyl cellulose, starches, microcrystalline cellulose, soy protein, alginic acid, crosslinked polyvinylpyrrolidone, crosslinked sodium carboxymethylcellulose and mixtures thereof.

9. A process for making an oral dosage form of a calcium dietary supplement composition, comprising compressing the directly compressible calcium dietary supplement composition of claim 4.

10. An oral dosage form of a calcium dietary supplement composition, made by compressing the composition of claim 4.

11. The oral dosage form of claim 10, wherein the oral dosage form exhibits a hardness of greater than or equal to 10 kilopond.

12. The oral dosage form of claim 10, wherein the oral dosage form exhibits a hardness of greater than or equal to 15 kilopond.

13. The oral dosage form of claim 10, wherein the oral dosage form exhibits a friability of less than 1%.

14. A chewable oral dosage form made by compressing a composition comprising a compressible tricalcium phosphate agglomerate, said compressible tricalcium phosphate agglomerate comprising, based on 100 pbw of the agglomerate, from about 90 to about 99 pbw tricalcium phosphate particles, each having an outer surface, and from about 1 to about 10 pbw a binder comprising a polyvinylpyrrolidone, carrageenan, guar gum, modified guar gum, or a mixture of guar gum and modified guar gum, supported on at least a portion of the outer surface of at least a portion of the tricalcium phosphate particles, and which agglomerate is made by spray drying an aqueous slurry comprising the tricalcium phosphate particles and the binder.

15. The oral dosage form of claim 14, wherein the oral dosage form exhibits a hardness of greater than or equal to 10 kilopond.

16. The oral dosage form of claim 14, wherein the oral dosage form exhibits a hardness of from about 12 to about 22 kilopond.

17. The oral dosage form of claim 14, wherein the oral dosage form exhibits a hardness of from about 14 to about 16 kilopond.

* * * * *